United States Patent [19]
Kelman

[11] Patent Number: 4,591,358
[45] Date of Patent: May 27, 1986

[54] INTRAOCULAR LENS

[76] Inventor: Charles D. Kelman, North Shore Towers, 269 Grand Central Pkwy., Floral Park, N.Y. 11005

[21] Appl. No.: 480,836

[22] Filed: Mar. 31, 1983

[51] Int. Cl.$^4$ ............................................... A61F 2/16
[52] U.S. Cl. ....................................................... 623/6
[58] Field of Search ................................... 3/13; 623/6

[56] References Cited

U.S. PATENT DOCUMENTS 4,418,431  12/1983  Feaster ........................................ 3/13
4,437,194   3/1984  Hahs ........................................... 3/13

OTHER PUBLICATIONS

American IOL International Intraocular Lenses (advertisement) American IOL International, 15542 Graham St., Huntington Beach, CA 92647, "Style 115 Shepard Universal A/C IOL", Dec. 29, 1981.
Lens Styles from Cilco (brochure), Cilco, Cilco, Inc., 1616 13th Ave., Box 1680, Huntington, West Virginia 25717, Oct. 1982, Multiflex Anterior Chamber Lens & Symmetrical Multiflex Anterior Chamber Lens.

Primary Examiner—Ronald L. Frinks
Attorney, Agent, or Firm—Henry Sternberg; Bert J. Lewen

[57] ABSTRACT

An intraocular lens suitable for seating in the ciliary sulcus of the posterior chamber of a human eye utilizing flexible legs individually making substantially single contact points with the interior of the eye and individually comprising compression springs.

9 Claims, 2 Drawing Figures

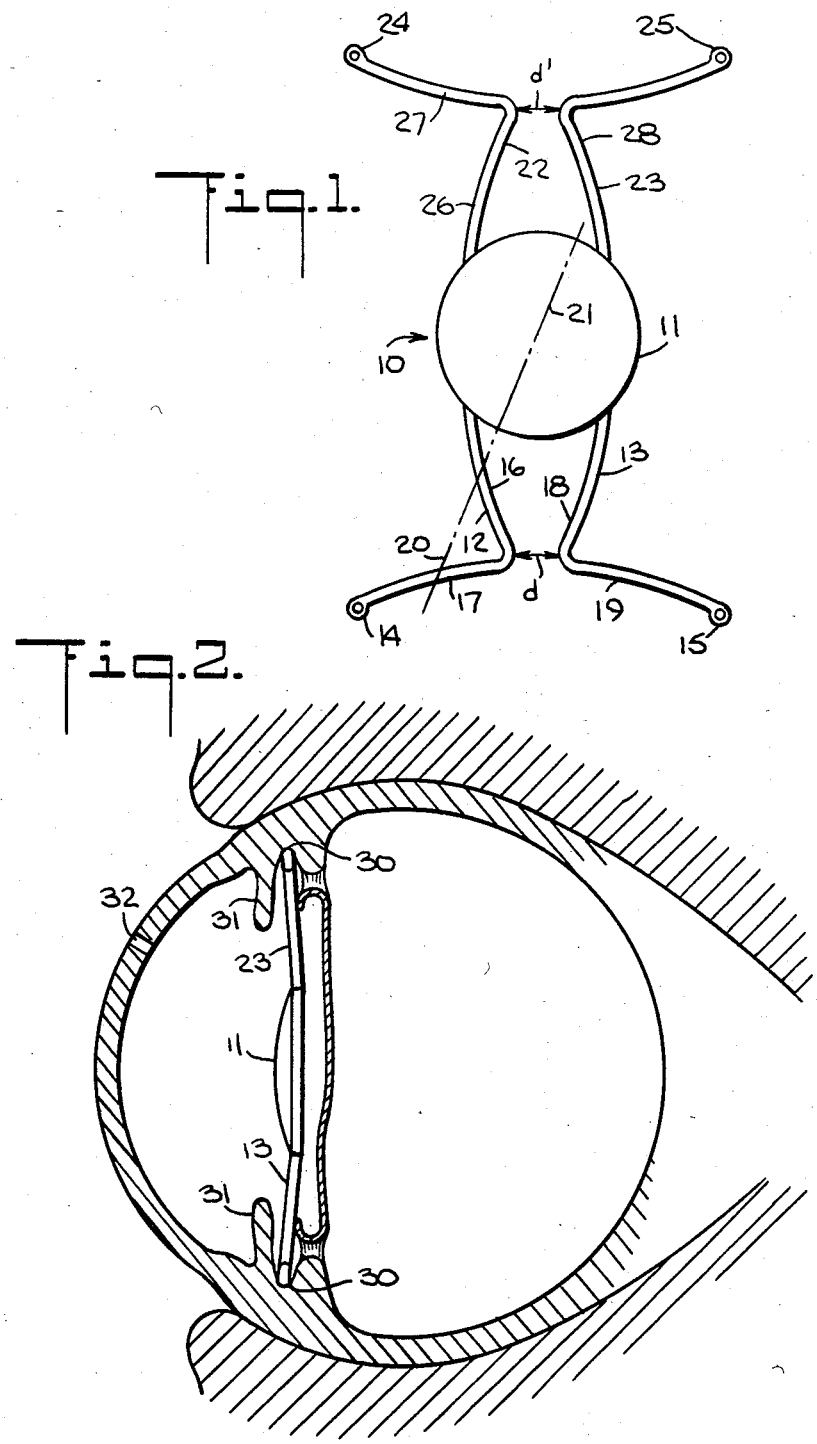

INTRAOCULAR LENS

This invention relates to intraocular lenses of the type suitable for use as an artificial lens in the interior of a human eye, and, more particularly, to intraocular lenses of the type suitable for use in the posterior chamber of the eye.

Heretofore, various lenses have been proposed for use in the anterior or posterior chamber. Prior lenses have generally not been suitable for seating in the ciliary sulcus of the posterior chamber because the position-fixation means of the lenses frequently damaged the tissues of the ciliary sulcus.

One prior lens has been proposed for seating in the ciliary sulcus of the posterior chamber with position-fixation means of polypropylene, which position-fixation means of polypropylene are sufficiently flexible for such seating. However, there are substantial concerns in the medical community about the biological inertness, the ability to resist aging, e.g., resistance to cracking, discoloration and stiffening, of polypropylene. Thus, there is the fear that the polypropylene position-fixation means of the lens referred to above may cause damage to the eye. Polymethylmethacrylate, on the other hand, is a material of proven biological inertness and good aging characteristics. Position-fixation means of this material, however, are not as flexible as position-fixation means of polypropylene and polymethylmethacrylate, therefore, was not believed to be useful for position-fixation means seating in the ciliary sulcus of the posterior chamber.

In my copending application Ser. No. 465,573 filed Feb. 10, 1983, I have described and claimed an intraocular lens which has position-fixation means which, even though made of polymethylmethacrylate or other suitable materials known in the art as being biologically inert and transparent for optical correction, are sufficiently flexible for seating in the ciliary sulcus of the eye.

It is an object of the present invention to provide a new and improved intraocular lens which avoids one or more of the disadvantages and limitations of prior such lenses.

It is another object of the invention to provide a new and improved intraocular lens which is suitable for use in the posterior chamber of the eye.

It is another object of the invention to provide a new and improved intraocular lens which is suitable for seating in the ciliary sulcus of the posterior chamber of the eye.

It is another object of the invention to provide a new and improved intraocular lens which has position-fixation means of greater flexibility than prior such lenses for seating in the ciliary sulcus of the posterior chamber of the eye.

In accordance with the invention, an intraocular lens suitable for use as an artificial lens in the interior of a human eye comprises a light-focusing lens body. The lens also includes first and second position-fixation means individually joined to the lens body and extending outwardly from the lens body for seating in interior portions of an eye. The first and second position-fixation means each have a single contact portion adapted to make substantially a single contact point with an interior portion of an eye. The first and second position-fixation means individually include portions extending from the lens body to the individual contact portions generally in at least two predetermined opposite senses with respect to the lens body to provide resilience of the contact portions with respect to the lens body. The intraocular lens also includes other position-fixation means joined to the lens body for positioning the lens in the interior of the eye.

For a better understanding of the present invention, together with other and further objects thereof, reference is made to the following description taken in connection with the accompanying drawings, and its scope will be pointed out in the appended claims.

FIG. 1 is a diagrammatic plan view of an embodiment of the present invention intended for fixation in the ciliary sulcus of the posterior chamber of the eye; and FIG. 2 is a side elevational view of the FIG. 1 lens positioned within the eye, shown in section.

Referring now more particularly to FIG. 1 of the drawings, an intraocular lens 10 suitable for use as an artificial lens in the interior of a human eye comprises a light-focusing body or optic 11. The optic 11 may be constructed of any biologically inert and transparent material for optical correction such as polymethylmethacrylate, quartz, opthalmic glass, and other materials known in the art. The lens includes first and second position-fixation means 12, 13 individually joined to the lens body 11 and extending outwardly from the lens body for seating in interior portions of an eye. The position-fixation means 12, 13 preferably are legs of polymethylmethacrylate.

The first and second position-fixation means 12, 13 each have a single contact portion 14, 15, respectively, adapted to make substantially a single contact point with an interior portion of an eye. The first and second position-fixation means 12, 13 individually include portions 16, 17 and 18, 19 extending from the lens body 11 to the individual contact portions 14, 15 generally in at least two predetermined opposite senses with respect to the lens body to provide resilience of the contact portions 14, 15 with respect to the lens body.

The first position-fixation means 12 extending from the lens body 11 to one of the contact portions 14 extends sequentially through portions 16, 17 in clockwise and counterclockwise senses, respectively, with respect to the lens body. The second position-fixation means 13 extending from the lens body 11 to another of the contact portions 15 extends sequentially through portions 18, 19 in counterclockwise and clockwise senses, respectively, with respect to the lens body 11.

The first and second position-fixation means 12, 13 extending from the lens body to the individual contact portions 14, 15, respectively, individually comprise compression springs.

An imaginary longitudinal extension 20 of a predetermined equator 21, each represented in broken-line construction, intersects, at least twice, the first position-fixation means 12 extending, through portions 16, 17, generally in at least two predetermined opposite senses with respect to the lens body 11.

The lens 10 also includes other position-fixation means joined to the lens body 11 for positioning the lens body in the interior of the eye. More particularly, the other position-fixation means 22, 23 joined to the lens body for positioning the lens in the interior of the eye. The third and fourth position-fixation means 22, 23 preferably are of similar construction to the second and first position-fixation means 13, 12, respectively The third and fourth position-fixation means 22, 23 each have a single contact portion 24, 25 adapted to make substantially a single contact point with an interior portion of an eye. The third and fourth position-fixation means 22, 23 individually include portions 26, 27 and 28, 29 extending from the lens body to the individual contact portions 24, 25, respectively, of the third and fourth position-fixation means 22, 23 generally in at least two predetermined opposite senses with respect to the lens body 11 to provide resilience of the contact portions of the third and fourth position-fixation means with respect to the lens body 11.

The minimum distance d between the first and second position-fixation means 12, 13 preferably is in the range of approximately 1 to 2 millimeters when said position-fixation means are in undeformed condition so as to permit free movement of the first and second position-fixation means toward one another in response to movement of the respective contact portions toward the lens body. Similarly, the minimum distance d' between the third and fourth position-fixation means preferably is in the range of approximately 1 to 2 millimeters. The lens body 11 may have a diameter of, for example, approximately five millimeters.

Each of the first and second position-fixation means 12, 13 has a free end portion and each free end portion thereof comprises each single contact portion 14, 15, respectively.

As represented in FIG. 2, by passing the lens 10 through the surgical opening 32, the surgeon may seat the position-fixation means in the ciliary sulcus 30 of the eye posteriorly with respect to the iris 31.

The portions 18, 19 of the position-fixation means 13 and the portions 28, 29 of the position-fixation means 23 provide sufficient resilience of the contact portions 15, 25 with respect to the lens body that the tissues of the ciliary sulcus are not damaged. Although not apparent in FIG. 2, the position-fixation means 12, 22 are seated in the ciliary sulcus in a manner similar to the position-fixation means 13, 23 shown.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. An intraocular lens suitable for use as an artificial lens in the interior of a human eye comprising:
   a light-focusing lens body;
   first and second position fixation means individually joined to said lens body and extending outwardly from said lens body for seating in interior portions of an eye;
   said first and second position-fixation means each having a single contact portion adapted to make substantially a single contact point with an interior portion of an eye, said first and second position-fixation means individually including portions extending from said lens body to said individual contact portions generally in at least two predetermined opposite senses with respect to said lens body to provide resilience of said contact portions with respect to said lens body; said portions of said first position-fixation means which extend from said lens body to one of said contact portions extending sequentially in clockwise and counterclockwise senses with respect to said lens body, and said portions of said second position-fixation means which extend from said lens body to another of said contact portions extending sequentially in counterclockwise and clockwise senses with respect to said lens body; and
   other position-fixation means joined to said lens body for positioning said lens body in the interior of the eye.

2. A lens in accordance with claim 1 in which said portions of said first and second position-fixation means extending from said lens body to said individual contact portions individually comprise compression springs.

3. A lens in accordance with claim 1 in which an imaginary longitudinal extension of a predetermined equator of said lens body intersects, at least twice, said portion of said first position-fixation means extending generally in at least two predetermined opposite senses with respect to said lens body.

4. A lens in accordance with claim 1 in which said position-fixation means are of polymethymethacrylate.

5. A lens in accordance with claim 1 in which said other position-fixation means includes third and fourth position-fixation means joined to said lens body for positioning said lens in the interior of the eye.

6. A lens in accordance with claim 5 in which said third and fourth position-fixation means each have a single contact portion adapted to make substantially a single contact point with an interior portion of an eye, said third and fourth position-fixation means individually including portions extending from said lens body to said individual contact portions of said third and fourth position-fixation means generally in at least two predetermined opposite senses with respect to said lens body to provide resilience of said contact portions of said third and fourth position-fixation means with respect to said lens body.

7. A lens in accordance with claim 1 in which the minimum distance between said first and second position-fixation means is in the range of approximately 1 to 2 millimeters when said first and second position-fixation means are in undeformed condition.

8. A lens in accordance with claim 1 in which each of said first and second position-fixation means has a free end portion and said each free end portion comprises said each single contact portion.

9. A lens in accordance with claim 1, said eye interior having an upper groove portion and a lower groove portion and said lens body having a first peripheral portion adapted to face the upper groove portion and a second peripheral portion opposite said first peripheral portion and facing the lower groove portion when the lens is seated in the eye, said first and second position-fixation means being individually joined to said lens body at the same one of said peripheral portions thereof.

* * * * *